US011690590B2

(12) United States Patent
Keidar (10) Patent No.: US 11,690,590 B2
(45) Date of Patent: Jul. 4, 2023

(54) NON-INVASIVE HEART VALVE SCREENING DEVICE AND METHOD (71) Applicant: Edwards Lifesciences Corporation, Irvine, CA (US)

(72) Inventor: Yaron Keidar, Haifa (IL)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 963 days.

(21) Appl. No.: 16/177,609

(22) Filed: Nov. 1, 2018

(65) Prior Publication Data
US 2019/0142363 A1    May 16, 2019

Related U.S. Application Data

(60) Provisional application No. 62/585,374, filed on Nov. 13, 2017.

(51) Int. Cl.
| A61B 8/06 | (2006.01) |
| A61B 5/00 | (2006.01) |
| A61B 8/08 | (2006.01) |
| A61B 8/00 | (2006.01) |
| A61B 7/02 | (2006.01) |

(52) U.S. Cl.
CPC .............. *A61B 8/06* (2013.01); *A61B 5/6823* (2013.01); *A61B 7/023* (2013.01); *A61B 8/08* (2013.01); *A61B 8/4427* (2013.01); *A61B 8/4455* (2013.01); *A61B 8/488* (2013.01); *A61B 8/5223* (2013.01); *A61B 8/56* (2013.01); *A61B 8/0883* (2013.01); *A61B 8/4488* (2013.01)

(58) Field of Classification Search
CPC ......... A61B 5/6823; A61B 7/023; A61B 7/04; A61B 8/06; A61B 8/08; A61B 8/0883; A61B 8/4427; A61B 8/4455; A61B 8/4488; A61B 8/488; A61B 8/5223; A61B 8/56; G16H 50/30
See application file for complete search history.

(56) References Cited

U.S. PATENT DOCUMENTS

| 5,817,024 A | 10/1998 | Ogle et al. | |
| 2002/0151795 A1* | 10/2002 | Palti | A61B 8/06 |
| | | | 600/455 |
| 2005/0165310 A1 | 7/2005 | Bindefeld | |

(Continued)

FOREIGN PATENT DOCUMENTS

| CN | 106510887 A | 3/2017 |
| JP | 2013135836 A | 7/2013 |
| JP | 2016105747 A | 6/2016 |

OTHER PUBLICATIONS

Kiruthika, et al., "Automated Assessment of Aortic Regurgitation using 2D Doppler Echocardiogram," International Workshop on Imaging Systems and Techniques, Minori, Italy, Apr. 29, 2006.

*Primary Examiner* — Michael T Rozanski (57) ABSTRACT

The invention is a device, system, and method for providing an initial assessment of potential heart valve disease and recommending and/or providing follow-up assessments for heart valve disease. The invention includes a simple ECHO device which uses ultrasonic signals to detect and determine maximum blood flow velocities, and compares the maximum blood flow velocities to set thresholds to determine if it is appropriate for the patient to be subjected to additional and more detailed assessments for heart valve disease.

4 Claims, 5 Drawing Sheets

(56) References Cited

U.S. PATENT DOCUMENTS

| | | | |
|---|---|---|---|
| 2009/0304625 A1* | 12/2009 | Husain | A61K 38/1875 424/85.2 |
| 2010/0049052 A1 | 2/2010 | Sharf et al. | |
| 2011/0092819 A1 | 4/2011 | Takimoto et al. | |
| 2013/0137987 A1 | 5/2013 | Abe et al. | |

* cited by examiner

NON-INVASIVE HEART VALVE SCREENING DEVICE AND METHOD

CROSS-REFERENCE TO RELATED APPLICATIONS

This application claims priority to U.S. Provisional Patent Application No. 62/585,374, filed Nov. 13, 2017, the contents of which are incorporated herein by reference in their entirety.

FIELD OF THE INVENTION

The present invention relates to screening patients for heart disease, and, more particularly, to methods and apparatuses for detecting heart valve malfunction by positioning a non-invasive monitoring device on the exterior chest wall.

BACKGROUND OF THE INVENTION

In vertebrate animals, the heart is a hollow muscular organ having four pumping chambers: the left and right atria and the left and right ventricles, each provided with its own one-way outflow valve. The natural heart valves are identified as the aortic, mitral (or bicuspid), tricuspid and pulmonary valves. The valves separate the chambers of the heart, and are each mounted in an annulus therebetween. The annuluses comprise dense fibrous rings attached either directly or indirectly to the atrial and ventricular muscle fibers. The leaflets are flexible collagenous structures that are attached to and extend inward from the annuluses to meet at coapting edges. The aortic, tricuspid, and pulmonary valves usually have three leaflets, while the mitral valve usually has two leaflets.

The operation of the heart, and thus the patient's health, may be seriously impaired if any of the heart valves is not functioning properly. Various problems can develop with heart valves for a number of clinical reasons. Stenosis in heart valves is a condition in which the valves do not open properly. Insufficiency is a condition which a valve does not close properly. Dysfunction of the aortic or mitral valves is most common because they reside in the left side of the heart where pressures and stresses are the greatest.

Heart valves may lose their ability to close properly due to dilation of an annulus around the valve or a flaccid, prolapsed leaflet. The leaflets may also have shrunk due to disease, such as rheumatic disease, thereby leaving a gap in the valve between the leaflets. The inability of the heart valve to close will cause blood to leak backwards (opposite to the normal flow of blood), commonly referred to as regurgitation. Common examples of such regurgitation include mitral valve regurgitation (i.e., leakage of blood through the mitral valve and back into the left atrium) and aortic valve regurgitation (i.e., leakage through the aortic valve back into the left ventricle). Regurgitation may seriously impair the function of the heart since more blood will have to be pumped through the regurgitating valve to maintain adequate circulation. Heart valve regurgitation decreases the efficiency of the heart, reduces blood circulation, and adds stress to the heart. In early stages, heart valve regurgitation leaves a person fatigued and short of breath. If left unchecked, the problem can lead to congestive heart failure, arrhythmias, or death.

Patients who are identified as having heart valve disease can receive treatments (such as valve repair and/or replacement) and/or additional monitoring of heart function, such as the remote/at-home monitoring system and method disclosed in pending U.S. Provisional Patent Application No. 62/579,709, filed Oct. 31, 2017 and entitled "Non-Invasive Wearable Heart Valve Monitor" (the entire contents of which are hereby incorporated herein by reference).

Early detection of heart valve malfunction, such as valve stenosis, is critical to proper patient care. However, heart valve disease such as valve stenosis tends to be largely underdiagnosed because full diagnosing is a complicated process which can involve expensive devices and methods. For example, complicated and expensive imaging systems such as an echocardiogram can be used to provide an image of the heart valve orifice and/or valve leaflets. Such imaging systems tend to be expansive and require extensive training by a user in order to properly operate the device and interpret the data provided. Using such systems can provide confirmation of the existence and extent of heart valve disease, but is generally impractical for use to routinely screen all patients.

A more effective method of using such expensive and complicated imaging and diagnosis systems is to reserve them for patients who are identified through preliminary screening as potentially having heart disease. However, the key to such effective use of the expensive/complicated systems is to provide an easy, inexpensive, and effective method and device for preliminary screening of the patients.

The most common method currently used to screen patients for potential valve stenosis is for the doctor to use a standard stethoscope applied to the patient in order to listen for a heart murmur, which is a soft whooshing or humming sound the blood makes as it passes through the narrowed opening of a stenotic valve. However, the doctor must have good hearing and be very well trained in order to audibly detect the heart murmur. Sometimes the murmur is very quiet, and even a well-trained physician may not be able to hear the murmur and distinguish it from background noises.

What has been needed is a small, low-cost, and low-power device that can be used by medical personnel with minimal training for screening patients for an indication of heart valve disease, with any screened patients exhibiting such initial indications of heart valve disease then sent to more complicated and expensive monitoring/imaging/analysis for full diagnosis of whether the patient has heart valve disease. The present invention fulfills this need.

SUMMARY OF THE INVENTION

The present invention provides an inexpensive and simple method for identifying patients who may be at high risk of having heart valve disease. The device and method of the invention can be used by medical personnel with relatively simple training. Devices according to the invention are small and inexpensive, so they can be on hand and available in any doctor's office.

Diseased heart valves often have increased blood flow velocities. For example, a stenotic heart valve typically has a smaller functioning orifice, and the reduced orifice size causes blood flow therethrough to travel at higher velocities than through healthy valves. High blood flow velocities in and of themselves are not sufficient to diagnose heart valve disease, but can be used to identify patients to recommend for further diagnosis. Thus, the peak flow velocity can be used to identify patients at high risk of heart valve disease, with the high risk patients then sent on to more expensive and complicated testing and analysis for full diagnosis.

Embodiments of the present invention involve an inexpensive hand-held device that can measure peak fluid flow velocities through heart valves using ultrasound. Note that it may not be necessary for the device to determine which valve is the source of the measured peak velocity—all that may be needed is to determine whether any peak blood flow velocity in the patient's heart exceeds levels indicating an elevated risk of heart valve disease. For example, the highest blood flow speeds are typically those created as the blood passes through the heart valves, and through stenotic valves in particular. Using the device on a patient, a doctor or other user can measure peak flow speeds that indicate low risk (e.g., less than 2.5 m/s), mild risk (e.g., 2.5 to 3 m/s), medium risk (e.g., 3 to 4 m/s), or high risk (e.g., greater than 4 m/s) of heart valve disease.

The present invention describes a system and method to identify peak blood flow velocities in a human heart, and to provide indicia to a user indicating the risk of the patient having heart valve disease. For example, the indicia may be a numerical readout of the peak blood flow velocity (e.g., in meters per second m/s), and/or be a low/mild/medium/high risk indicator (e.g., green/yellow/orange/red light).

Echo Doppler ultrasound can be used to determine the blood flow velocity through the valves. The relative velocity of the blood towards the ultrasound transducer or away from it is detected as a frequency shift of the ultrasonic echo reflected from the blood. Modern ultrasound systems use phased arrays of ultrasound transducers and can differentiate echo signals by the direction from which the signals are coming. The operator can point a cursor to a structure in the ultrasound image (e.g., the center of a specific heart valve) and the phased array will separate the echo coming from that location and analyze blood velocity there. Such phased arrays can provide data that can be processed to create images of the heart and local blood flows, but require trained operator input and assessment and are relatively complex and expensive, and often require relatively high power levels.

A small and inexpensive echo device can be used not for complicated imaging or blood flow analysis but instead simply to identify peak blood flow velocities, which can be achieved using a relatively broad ultrasound beam to identify the fastest fluid flow within the beam field. The device may include a transducer configured to provide the relatively broad ultrasound beam, such as a discrete transducer (e.g., a discrete piezo-electric transducer). A power source, such as a battery and/or power cord, may be provided. A simple processor may be configured to receive transducer data and calculate peak blood flow velocity (using well-known echo Doppler calculations), and a memory and display may store and display the highest peak blood flow velocity measured by the device.

Various dimensions and configurations of the device are within the scope of the invention. The device may preferably be sized and dimensioned to easily be held in the hand of a user while being run across the surface of a patient's skin, typically in the chest and abdominal areas. The device can also be sized to house one or more echo transducers, with typical transducers for use with the device often have dimensions of 1 to 3 cm in diameter. In some embodiments, the main body may have length of 1 to 10 cm or 4 to 7 cm, width of 1 to 6 cm or 3 to 5 cm, and thickness of 1 to 4 cm or 2 to 3 cm. The device may have a handle portion configured to be grasped by a user (such as a physician or nurse), and a patient-facing portion configured to be applied against the chest/abdomen of a patient. The patient-facing portion may comprise a relatively smooth and/or flat surface, with the ultrasonic beam directed out of the surface of the patient-facing portion.

The power source may comprise a battery configured for inductive recharging. The power source, processor, and/or transducers may be enclosed in a waterproof casing. Each of the discrete transducers may be a discrete piezo-electric transducer.

A system for screening patients for heart valve disease according to an embodiment of the invention includes a monitor device configured to be placed against and moved around on a chest of a patient, with the device having: a main body comprising a hand-held portion and a patient-facing surface; a transducer configured to transmit ultrasonic sound outward from the patient-facing surface; a processor configured to transducer data and to calculate heart valve blood velocities using the transducer data; indicia of blood flow velocities (such as a digital display or warning light or warning sound/speaker); and/or a power supply. The system may further include a wireless transmitter and/or a cell phone, wherein the cell phone is configured to receive heart valve blood flow data from the wireless transmitter (e.g., Bluetooth transmitter/receiver) of the device. The cell phone may be configured to communicate via a cellular network or an internet connection. The system may include a remote computer, where the remote computer is in communication with the cell phone via the cellular network and/or the internet connection. The remote computer may receive heart valve blood flow velocity data from the cell phone via the cellular network or internet connection. The power supply may comprise a battery (which may be rechargeable via a cord or inductively) and/or wired plug-in for plugging into a wall power outlet.

The hand-held echo velocity monitoring device may comprise a stethoscope and simple ECHO device in combination. The ECHO device may be built-in to the stethoscope, such as where the ultrasonic beam is directed out of the patient-facing diaphragm of the stethoscope. The ECHO device may be configured to be removably secured to a stethoscope, such as by being slide onto an outside structure of the stethoscope.

Methods according to the invention may include moving a simple ECHO device over the patient's chest, such as moving the device to a position as close to the alignment with the heart valve orifices (such as by placing the device in or close to alignment with a central axis of the heart, with the heart central axis defined as a line passing from the heart apex a point between the aortic and mitral valves). The method may include determining a value for the valve flow velocity of the patient, including collecting ultrasonic data indicating valve flow velocity and calculating valve flow velocity therefrom; storing the calculated valve flow velocity value as a stored valve flow velocity in the memory; replacing the stored valve flow velocity value in the memory with each newly-calculated valve flow velocity value that exceeds the previously-stored valve flow velocity value; and repeatedly moving the device around on the patient's chest while collecting ultrasonic data and calculating via the processor new values for valve flow velocity in order to determine a peak blood flow velocity.

The method may include listening to the patient's heart, such as via a stethoscope (which may be a part of the device of the invention), to attempt to detect sounds associated with a heart murmur.

Applying the device to the patient's chest/abdomen may include positioning the transducer on the patient's chest/abdomen aimed in a first transducer direction wherein the first transducer direction is believed to be close in alignment to a flow axis of one or more heart valves; determining blood flow velocities from that position on the patient's chest/ abdomen; and repositioning the transducer at subsequent positions on the patient's chest/abdomen and determining blood flow velocities from each of those positions on the patient's chest/abdomen. Positioning the device on the patient's chest may include positioning the device adjacent or lower than the apex of the patient's heart. Positioning the device on the patient's chest may include positioning the device on or adjacent the crease between the pectoral muscle/breast and the abdominal muscles.

Methods of screening a patient for heart valve disease according to the invention may include detecting peak blood flow velocity within the heart using the hand-held echo velocity monitoring device of the invention; comparing the peak blood flow velocity to a determined threshold value; and if the peak blood flow velocity is determined to exceed a determined threshold, then recommending the patient for additional heart valve disease assessment and analysis using equipment other than the hand-held echo monitoring device. If the peak blood flow velocity is determined to be below the predetermined threshold, the patient may not be recommended for or provided with additional heart valve disease assessment and analysis (e.g., using equipment other than the hand-held echo monitoring device). Detecting peak blood flow velocity within the heart comprises moving the hand-held echo velocity monitoring device across multiple positions on the patient's chest and/or abdominal areas and detecting blood flow velocities while the hand-held echo velocity monitoring device is at each of the multiple positions. The hand-held echo velocity monitoring device may comprise a stethoscope and simple ECHO device in combination, where the ECHO device is built-in to the stethoscope or removably secured to the stethoscope.

The determined threshold value may be a predetermined value provided to the user, and/or may be selected by the user, such as by selecting the threshold based on patient-specific parameters such as overall patient health, patient medical history, patient family medical history, etc. The determined threshold value may be 2.5 m/s; 3.0 m/s; 3.5 m/s; 4.0 m/s; 2.5 m/s or more; 3.0 m/s or more; 3.5 m/s or more; 4.0 m/s or more; between 2.5 and 3.0 m/s; between 3.0 and 4.0 m/s.

The additional heart valve disease assessment and analysis include heart valve imaging via echocardiogram; heart valve imaging via magnetic resonance imaging (MRI); cardiac catheterization; stress testing; electrocardiogram (EKG); and/or chest x-ray. The additional heart valve disease assessment and analysis may include imaging of specific heart valve structures such as the heart valve orifice and/or valve leaflets.

Other objects, features, and advantages of the present invention will become apparent from a consideration of the following detailed description.

DETAILED DESCRIPTION OF SEVERAL EMBODIMENTS

Figure 1:
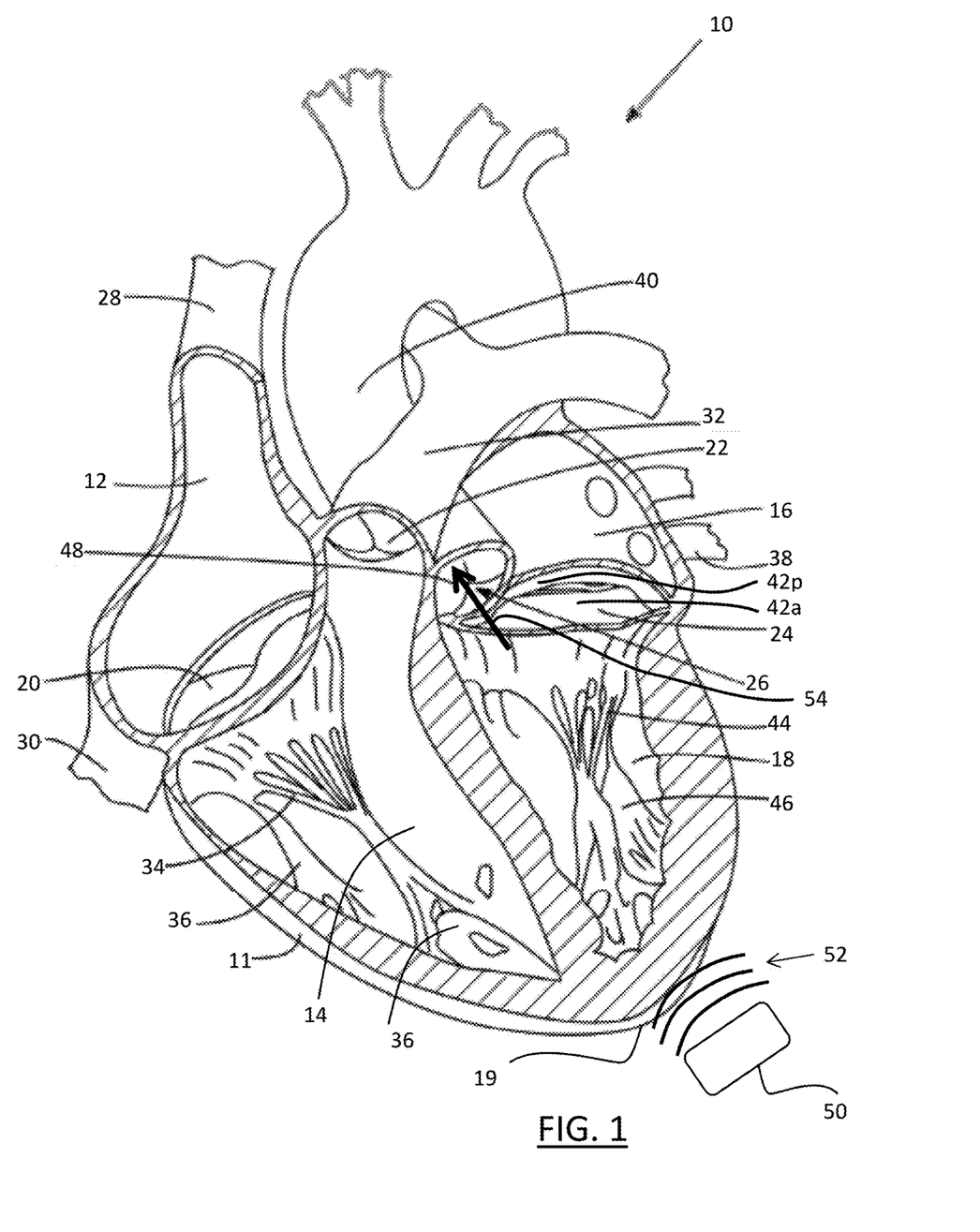
FIG. 1 is a cross-sectional view of a heart with a device positioned near the heart toward the apex thereof.

A cross-sectional view of a human heart 10 is depicted in FIG. 1. The heart 10 has a muscular heart wall 11, an apex 19, and four chambers: right atrium 12; right ventricle 14; left atrium 16; and left ventricle 18. Blood flow is controlled by four main valves: tricuspid valve 20; pulmonary valve 22; mitral valve 24; and aortic valve 26. Blood flows through the superior vena cava 28 and the inferior vena cava 30 into the right atrium 12 of the heart 10. The right atrium 12 pumps blood through the tricuspid valve 20 (in an open configuration) and into the right ventricle 14. The right ventricle 14 then pumps blood out through the pulmonary valve 22 and into the pulmonary artery 32 (which branches into arteries leading to the lungs), with the tricuspid valve 20 closed to prevent blood from flowing from the right ventricle 14 back into the right atrium. Free edges of leaflets of the tricuspid valve 20 are connected via the right ventricular chordae tendinae 34 to the right ventricular papillary muscles 36 in the right ventricle 14 for controlling the movements of the tricuspid valve 20.

After leaving the lungs, the oxygenated blood flows through the pulmonary veins 38 and enters the left atrium 16 of the heart 10. The mitral valve 24 controls blood flow between the left atrium 16 and the left ventricle 18. The mitral valve 24 is closed during ventricular systole when blood is ejected from the left ventricle 18 into the aorta 40. Thereafter, the mitral valve 24 is opened to refill the left ventricle 18 with blood from the left atrium 16. Free edges of leaflets 42*a*, 42*p* of the mitral valve 24 are connected via the left ventricular chordae tendinae 44 to the left ventricular papillary muscles 46 in the left ventricle 18 for controlling the mitral valve 30. Blood from the left ventricle 18 is pumped through the aortic valve 26 into the aorta 40, which branches into arteries leading to all parts of the body except the lungs. The aortic valve 26 includes three leaflets 48 which open and close to control the flow of blood into the aorta 40 from the left ventricle 18 of the heart as it beats.

A device 50 according to an embodiment of the invention is depicted in FIG. 1 positioned adjacent and/or below the heart apex 19 and providing ultrasonic pulses 52 directed toward the heart valves. The ultrasonic pulses pass through and are reflected back through the blood flow 54 through the heart valves, with the device 50 calculating the peak blood flow velocity detected. The device 50 may preferably not use the ultrasonic data to create echocardiogram images of the heart structures, as such displays require skilled operator input and assessment and are relatively complex and expensive, as well as requiring relatively high power levels.

A key element of the invention is measuring peak blood flow velocity in the heart valves (e.g., the aortic and/or mitral valves) using echo Doppler via the device using a simple ultrasound transducer or transducers held against and moved across the patient's chest, and providing a readout or other indicia of the peak blood flow velocity to a user such as doctor.

Figure 2:
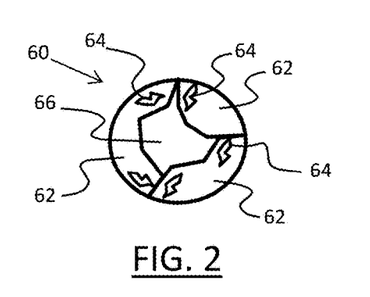
FIG. 2 depicts a top view of a stenotic heart valve.

FIG. 2 depicts a stenotic heart valve 60 in its most open configuration, which in the particular embodiment depicted is a stenotic aortic valve. The heart valve leaflets 62 are restrained in movement by calcified deposits 64, which restrict movement/flexibility of the heart valve leaflets 62 and thus reduce the effective size of the valve orifice 66 when the valve leaflets 62 are in their most open position. Blood flow is sped up significantly as it is compressed to pass through the constrained orifice 66.

Figure 3A:
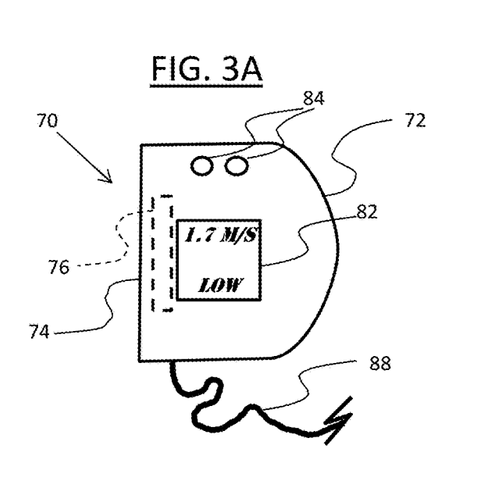
FIGS. 3A-3C depict top, side, and end views, respectively, of a device according to an embodiment of the invention.
Figure 3B:
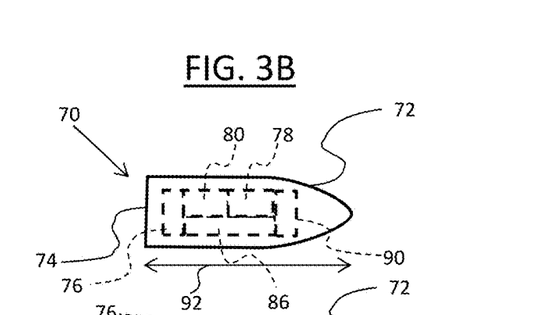
Figure 3C:
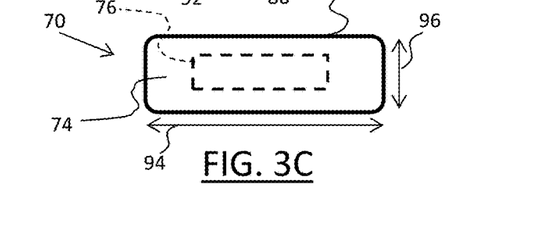

As depicted in FIGS. 3A-3C, a device 70 according to the invention has a main body 72 and a patient-facing surface 74. The main body 72 is sized and shaped to be comfortably held in a user's hand while the user applies the patient-facing surface 74 to the skin of a patient. A transducer 76 is positioned at or within the device 70, with the transducer 76 configured to transmit and receive ultrasonic pulses away from and into the patient-facing surface 74. A processor 78 is configured to receive the returned signals form the transducer 76, and to calculate a peak measured blood flow velocity form the returned signals using known Doppler techniques. The highest peak measured blood flow velocity value or values are stored in a memory 80, and may be displayed to the user via a display 82. Controls are provided 84 by which the user can activate the device 70. Power is provided by a power supply such as a battery 86 (which may be rechargeable) and/or power cord 90. The transducer 76 may preferably provide a relatively wide ultrasonic beam, with the device (e.g., processor) configured to determine the fastest thing moving within the field of view of the ultrasonic beam. The device 70 may include a communications system 90 configured to transmit and potentially receive information, such as a wireless transmitter and/or receiver, and/or a wired/corded communication link (such as a USB port for receiving a cord).

The device 70 may preferably be configured to be easily held in the user's hand and moved across the skin surface of a patient. To facilitate the ease of use and being grasped by the user, the device 70 may have dimensions such as a length 92 between 1 and 10 cm, width 94 between 1 and 6 cm, and thickness 96 between 1 and 3 cm. The device 70 may preferably have rounded corners, particularly on the patient-facing side that will be pressed against the patient's skin. The device 70 may preferably be operated in a cordless configuration (e.g., relying on battery power) for ease of use.

Figure 4A:
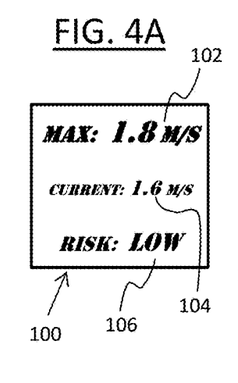
FIGS. 4A-4D depict top views of displays according to various embodiments of the invention.

FIGS. 4A-4D depict views of example displays according to embodiments of the invention. In FIG. 4A, a numerical display 100 includes a highest peak velocity value 102 (e.g., in meters/second, etc.) presented to the user. The numerical display 100 may also include a currently-measured velocity value 104, as well as a word 106 indicating the risk (e.g., "LOW") suggested by comparing the numerical value of the maximum peak velocity to a range of values for each risk level.

Figure 4B:
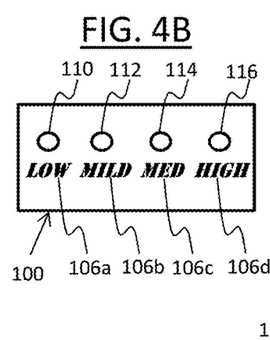

FIG. 4B depicts symbolic (non-word) indicia of patient risk for heart valve stenosis, which in the particular embodiment includes a green light 110 indicating low risk (which may correspond to a maximum blood flow rate that is below a mild risk velocity threshold, such as less than 2.5 m/s), a yellow light 112 indicating mild risk (which may correspond to a maximum blood flow velocity that is at or above a mild risk threshold such as 2.5 m/s but below a medium risk threshold such as 3.0 m/s), an orange light 114 indicating medium risk (which may correspond to a maximum blood flow velocity that is at or above a medium risk threshold such as 3.0 m/s but below a high risk threshold such as 4.0 m/s), and a red light 116 indicating high risk (which may correspond to a maximum blood flow velocity that is at or above a high risk threshold such as 4.0 m/s). Note that FIG. 4B also includes one or more words 106a, 106b, 106c, 106d indicating the risk (e.g., "LOW"), which may be indicated with a changeable letter display or be permanent (e.g., embossed lettering "LOW" adjacent a green light, "MEDIUM" adjacent a yellow light, "HIGH" adjacent a red light).

Figure 4C:
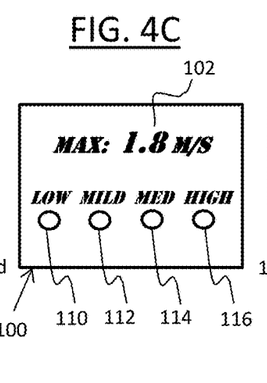

FIG. 4C depicts a combination of a numerical display for maximum detected flow velocity 102 along with symbolic indicia in the form of lights 110, 112, 114, 116, which in the embodiment depicted correspond to low, mild, medium, and high risk.

Figure 4D:
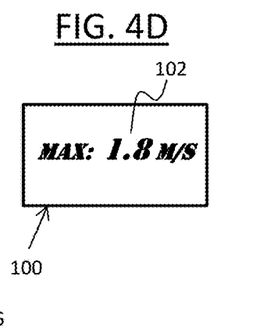

FIG. 4D simply depicts a numerical display for the maximum detected flow velocity 102, which may be desired due to the simple readout which provides only a single value for which the doctor or other user can interpret based on various factors specific to the particular patient, such as other risk factors for stenotic valve. For example, if the patient has been previously diagnosed with a stenotic valve and has previously had more complicated stenotic valve assessments performed (such as EKG and full ECHO imaging, etc.), then during a follow-up examination with the current device the doctor may consult the patient's history for prior readings of maximum detected flow velocity. If the doctor can see from prior maximum velocity readings taken on previous occasions (e.g., days or months or even years prior) that the patient's maximum blood flow velocity has not increased with the current reading, then the doctor may reasonably conclude that the patient does not require a follow-on EKG and/or full ECHO imaging at this time.

Note that other displays are also within the scope of the invention, such as a simpler symbolic display that may only include a single light, such as a red light, which if illuminated indicates an elevated risk. Another display might be a single light that flashes more rapidly for higher risks. Note that other elements and methods for providing risk information to the user are also within the scope of the invention, such as using acoustic feedback (e.g., beeping or other warning sounds) or vibrations to inform the user of the risk of the patient having a stenotic valve.

Figure 5:
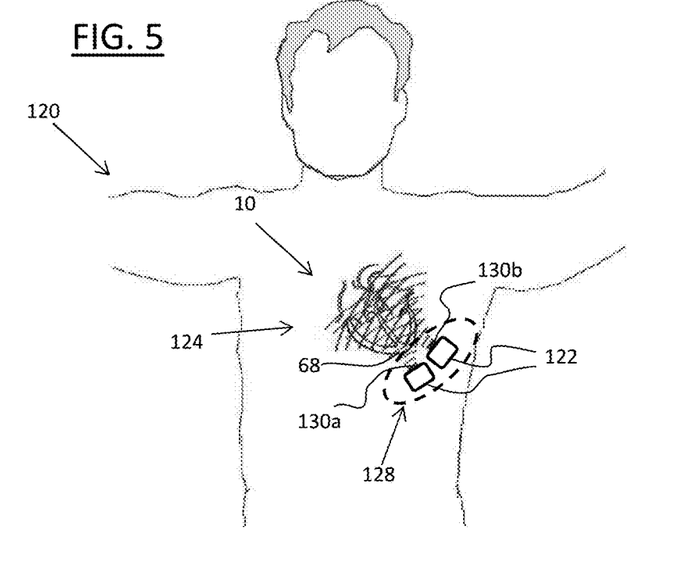
FIG. 5 depicts a front view of a patient with a device according to an embodiment of the invention.
Figure 6A:
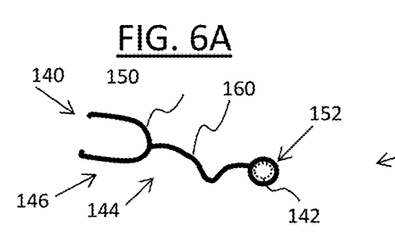
FIGS. 6A-6D depict perspective, side close-up, front close-up, and top close-up views, respectively, of a device according to an embodiment of the invention.
Figure 6B:
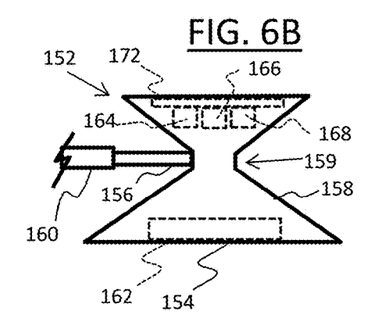
Figure 6C:
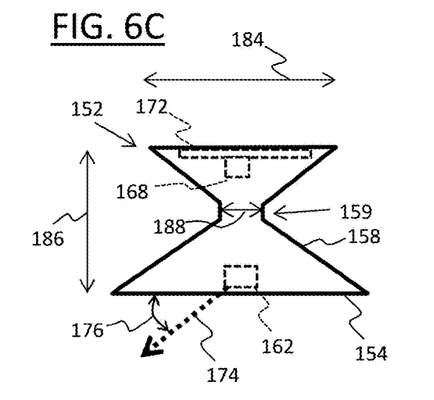
Figure 6D:
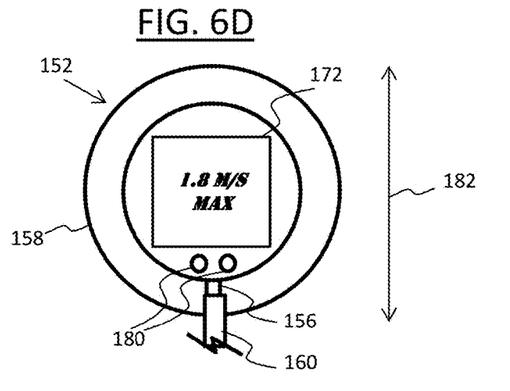

Methods of use of the device may depend on the particular application, including the particular heart valve and condition being assessed as well as the particular patient as well as the particular preferences of the particular user/doctor. However, for general assessment/screening of a patient for a stenotic heart valve, some methods of the invention can be almost universally applied. FIG. 5 depicts a patient 120 with a heart 10 having a device 122 of the invention positioned on and moved around on the patient's chest 124 to different positions 130a, 130b, etc. adjacent the heart apex 68 according to an embodiment of the invention. The device 122 may be moved in a slow scanning pattern over the patient 120 to cover most or all of the general area 128 on the patient that is below and adjacent the heart apex 68. The device 122 produces an ultrasonic beam directed toward one or more heart valves of the patient. Using the resulting ultrasonic data, the device 122 calculates the peak blood flow velocity detected using known Doppler techniques. Peak aortic flow velocity occurs in systole and its direction is negative (away from the device 122 on the chest 124), while peak mitral flow velocity occurs in diastole and its direction is positive (towards the device 122 on the chest 124). Traditional Doppler techniques can provide velocity readings for the blood flow through each of the valves, whether away from or toward the device 122.

Each different position 130a, 130b, etc., of the device 122 provides an ultrasonic beam at slightly different angles with respect to the heart. The respective measured peak blood flow velocities from each position 130a, 130b, etc. are calculated, with the highest of all the blood flow velocities provided to the user (e.g., doctor) via display or other indicia of maximum peak blood flow velocity Because the blood jets of one or more of the different heart valves (e.g., mitral or aortic or tricuspid or pulmonary) may be at an angle to the transducer(s) of the device in any one position of the device, and not directly towards or away from the transducer(s), the device can be moved across the patient's body (e.g., across the patient's chest/abdomen, such as at positions below the heart apex and/or along the crease between the chest and the abdomen) in order to calculate blood flow velocities using multiple angles. Note that the user can position the hand-held device in a first position on the patient's chest/abdomen, take first blood flow velocity measurements, then move the device to a second position and take second blood flow velocity measurements, then move the device to a third position, etc.

The user can watch the display of peak velocity from the device as the device is being moved across the patient's body, and modify movement of the device accordingly. For example, if movement of the device in a first direction results in the calculated blood flow velocity value increasing, the use can continue moving the device in that first direction. If the peak blood flow value decreases as the device is moved in the first direction, the user can move the device in a second direction (which may be opposite to the first direction) and again monitor the blood flow velocity reading to see if it is increasing or decreasing. The user may also (or alternatively) move the device around on the patient in the general area adjacent and below the heart apex in a manner to cover all or most of the area adjacent and immediately below the heart apex. The process is repeated until the user is satisfied that the highest peak blood flow velocity has been measured.

In a method of the examination, if the detected peak blood flow velocity exceeds a set threshold, then the doctor recommends the patient for (and/or provides the patient with) additional detailed analysis/assessment of heart valve condition, which may include detailed heart valve imaging, etc. Various thresholds are within the scope of the invention, such as 2.5 m/s (which may indicate a mild threat), 3.0 m/s (which may indicate a medium threat), or 4.0 (which may indicate a high threat).

Note that the particular threshold may be selected by the doctor based on patient-specific parameters. For example, if a patient has additional risk factors (such as family history and/or personal history of heart valve issues, high blood pressure, obesity, etc.), then the doctor may recommend the patient for detailed follow-on valve analysis/assessment based on a relatively low threshold being exceeded, whereas a patient with no or only a few additional risk factors may only be recommended for additional screening if the maximum blood flow velocity exceeds a higher threshold. Also, if the patient previously exceeded a first threshold but a follow-on detailed valve analysis/assessment (such as a detailed heart valve imaging) detected no heart valve anomalies, the doctor may set a higher (second) threshold for that particular patient for any subsequent examinations with the device of this invention—and the doctor may only recommend the particular patient for a follow-on detailed valve analysis/assessment/imaging if the maximum blood flow of the patient is determined to have increased from the previous screening examination that was conducted using the device and method of this invention.

A device 140 according to an embodiment of the invention is depicted in FIGS. 6A-6D, where the device 140 includes an ultrasonic portion 142 for velocity determination combined with a stethoscope portion 144. The stethoscope portion 144 has a headset 146 with ear tube 148 and eartips 150, as well as a chestpiece 152 with a diaphragm 154 and stem 156 and two-sided housing 158 having a neck portion 159. Tubing 160 connects the chestpiece 152 to the headset 146 and serves as a passage for acoustic signals received by the diaphragm 154. The ultrasonic portion 142 is on and in the chestpiece 152, and has a transducer 162, processor 164, memory 166, power supply 168, controls 170, and display 172. The transducer 162 may be positioned and configured in or on the chestpiece 152 to provide ultrasonic signals 174 in a direction or directions at an angle 176 between 0 and 90 degrees of the plane passing through the diaphragm 154. The angle 176 may typically be close to 90 degrees, but the ultrasonic signals 174 may preferably comprise a beam which is wide enough to cover the heart valves even if the center of the beam is not directed straight at the heart valves.

Note that ultrasonic elements such as the display 172 and transducer 162 may be rotatably movable with respect to the stem 156 and tubing 160, such as by rotating the stem 156 about the other portions of the chestpiece 152 through rotating arc 180. Such rotatable movement can permit the user to reposition the transducer 162 and/or display 174 for more convenient viewing of the display 162 and/or preferred direction of the transducer signals 174, depending on the particular user's preference in holding/using a stethoscope. The device dimensions may be similar or the same as traditional stethoscopes, such as a lower surface diameter 182 (which is also the overall diameter in the embodiment depicted) of 4 to 6 cm, upper surface diameter 184 of 3 to 5 cm, overall thickness 186 of 2 to 4 cm, and neck diameter 188 of 1 to 3 cm.

A device 190 according to an embodiment of the invention is depicted in FIGS. 7A-7F, where the device 190 includes an ultrasonic device 192 which is separate from but configured to be removably secured to a stethoscope 194 via connecting elements 196 such as a slot 198 configured to receive one or more portions of the stethoscope chestpiece 200. The user (e.g., doctor) can thus use his or her own preferred stethoscope 194 and simply attached the ultrasonic device 192 to the stethoscope 194. The ultrasonic device 192 has a transducer 202, processor 204, memory 206, power supply 208, controls 210, and display 212. The ultrasonic device 192 may include a patient-facing surface 214 out of which the transducer 202 can project a beam of ultrasonic pulses 216, which may be provided in a direction or directions at an angle 218 between 0 and 90 degrees of a plane passing through and parallel to the stethoscope diaphragm 220 and/or at an angle 222 from the plane of the patient-facing surface 214. The angles 218 and/or 222 may typically be close to 90 degrees, but the ultrasonic signals 216 may preferably comprise a beam which is wide enough to cover the heart valves even if the center of the beam is not directed straight at the heart valves.

The ultrasonic device 192 may be inexpensive and disposable, so that it can be used once or a few times and then thrown away. The transducer 202 may be positioned and configured such that, when the ultrasonic device 192 is secured to a stethoscope 194, ultrasonic signals are provided in a direction or directions between 0 and 90 degrees of the plane passing through the diaphragm 214 and/or in a direction or directions between 0 and 90 degrees of the plane passing through the patient-facing surface. The ultrasonic device 192 may be configured to be positioned and repositioned at various positions 216a, 216b around the chestpiece 200, per the preferences of a particular user.

Figure 7A:
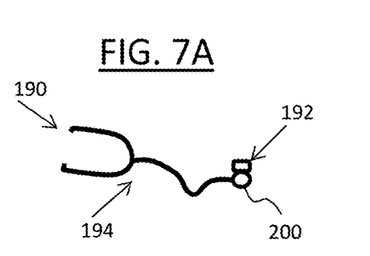
FIG. 7A depicts a perspective view of an ECHO device secured to stethoscope according to an embodiment of the invention.
Figure 7B:
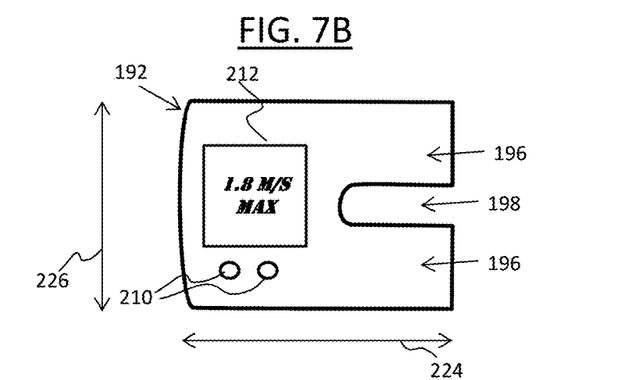
FIGS. 7B-7D depict top, side, and bottom, side close-up, and top close-up views, respectively, of a device according to an embodiment of the invention.
Figure 7C:
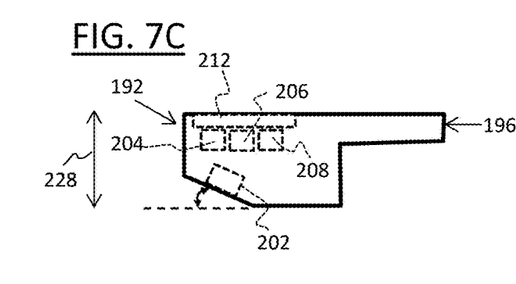
Figure 7D:
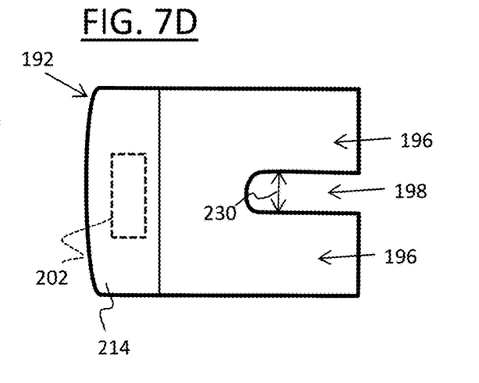
Figure 7E:
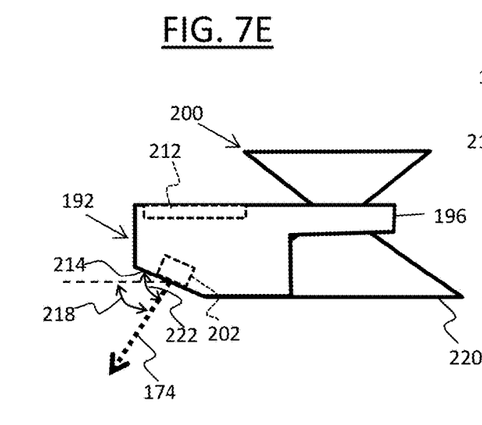
FIGS. 7E-7F depict side and top views of the device of FIGS. 7B-7D secured to a stethoscope according to an embodiment of the invention.
Figure 7F:
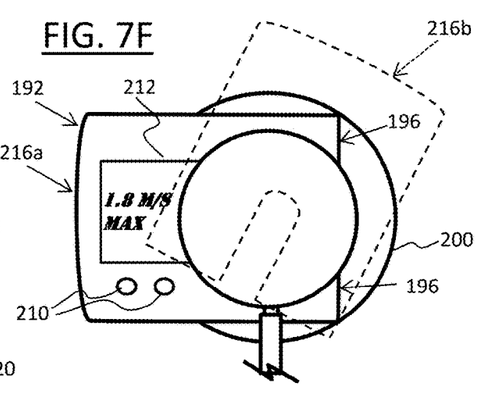

The device 192 may preferably have dimensions to coordinate its securement to a stethoscope chestpiece, such as having dimensions approximating those of the stethoscope chestpiece. Dimensions of preferred embodiments may include a length 224 of 4 to 7 cm, width 226 of 3 to 6 cm, and thickness 228 of 1.5 to 4 cm. The slot width 230 of 1 to 3 cm may be dimensioned to accommodate the neck portion of the stethoscope chestpiece.

Figure 8A:
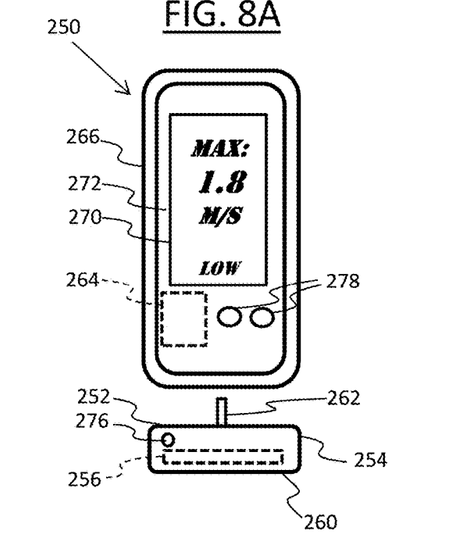
FIGS. 8A and 8B depict front views of a device and smart phone, in exploded (FIG. 8A) and connected (FIG. 8B) configurations, according to an embodiment of the invention.
Figure 8B:
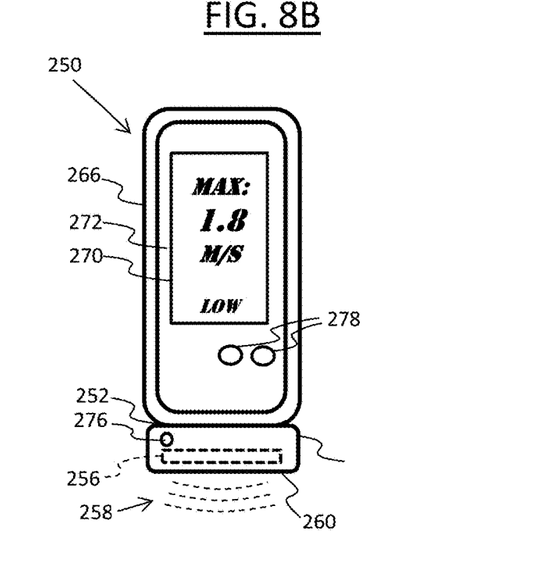

Further embodiments of the invention are depicted in FIGS. 8A-8D. In FIGS. 8A-8B, a system 250 has a small echo element 252 having a main body 254 with a transducer 256 directing ultrasonic beams 258 out of a patient-facing surface 260. Transducer data is provided via a plug connection 262 to an external processor 264 located inside a portable electronic device 266 such as a smart phone or tablet. The portable electronic device 266 may have internal programming, such as a dedicated mobile app, with which the processor 260 uses the transducer data, determines blood flow velocities, determines peak blood flow velocity, compares the peak blood flow velocity to set blood flow velocity thresholds, and provides data for a visual display of the results of the analysis/calculations. The portable electronic device 266 can provide a visual display, via its screen 270, of the currently measured high blood flow velocity, the peak blood flow velocity measured so far in the procedure, and/or the risk of the patient having heart valve disease/malfunction. The visual display may include displays of information such as those depicted in FIGS. 4A-4D.

Note that the echo device 252 may only provide transducer data to the external processor/portable electronic device 266, so that all data analysis is performed by the portable electronic device 266, such as in a dedicated mobile app uploaded to the portable electronic device 266. The portable electronic device 266 may also provide the indicia 270 of the patient's risk, which the user may view on the screen 272 of the portable electronic device. The portable electronic device 266 may also store the raw data provided by the transducer, and/or store (in internal memory) and/or upload (to external memory/internet/other remote devices) some or all of the various data, calculations (e.g., peak flow velocities), and comparisons/risk assessment data. Alternatively, the device 250 itself may have an internal processor (not shown) that performs some or all of the data analysis, including calculating the measured blood flow velocities, determining peak flow velocity, and comparing the peak flow velocity to the one or more thresholds.

Figure 8C:
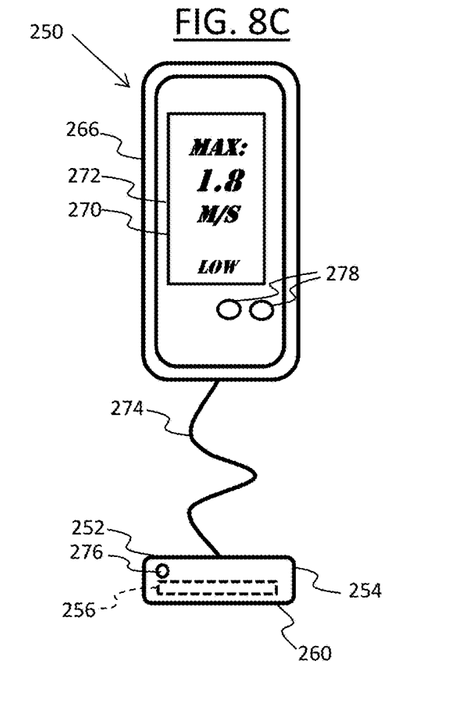
FIG. 8C depicts a device secured to a smart phone via a wired connection according to an embodiment of the invention.

In the embodiment of FIG. 8C, transducer data is provided to the external processor 264/portable electronic device 266 via a wired connection/cable 274, where the wired connection/cable 274 may be flexible and may have sufficient length for the portable electronic device to remain stationary with respect to the user and/or stationary within the room (such as on a nearby table) while the user's moves the echo device 252 across the patient to measure the blood flow velocities.

The echo device 252 may include one or more controls 276 with which the user can activate and/or otherwise control the echo device 252, although control may be provided solely via the portable electronic device 266 (e.g., via touchscreen controls 278 provided via the mobile app), particularly where the echo device 252 is connected via wire/cable or plug-in to the portable electronic device as in FIGS. 8A-8C.

Figure 8D:
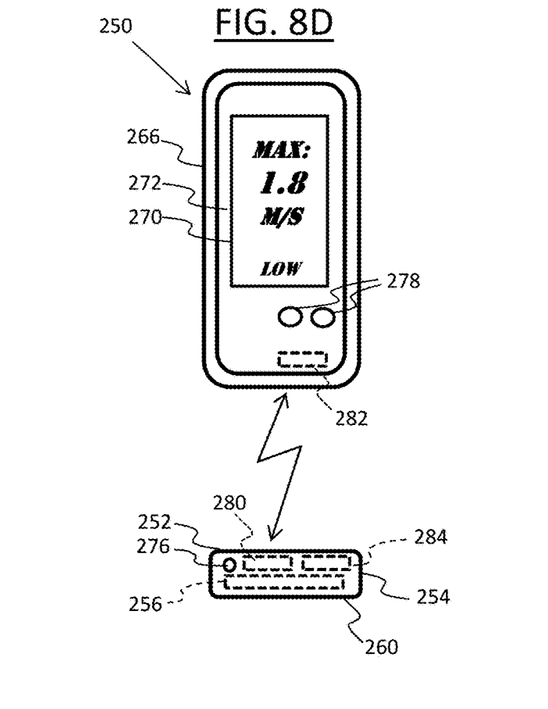
FIG. 8D depicts a device wirelessly transmitting to a smart phone according to an embodiment of the invention.

Transducer data may be provided to the external processor 264/portable electronic device 266 wirelessly (e.g., Bluetooth) from the echo device 252 via wireless components 280/282 on or in the echo device 252 and portable electronic device 266, as depicted in FIG. 8D.

Note that if the echo device 252 is secured via wire/cable or plug-in to the portable electronic device 266, as depicted in FIGS. 8A-8C, then the echo device 252 may rely on the portable electronic device 266 for power and may not need an internal battery within the echo device 252 itself. In a wireless configuration such as depicted in FIG. 8D, the echo device 252 will typically require an internal battery 284.

Note that the wireless embodiment of FIG. 8D may be particularly well suited to being configured to be removably secured to the chestpiece of a stethoscope, similar to the device depicted in FIGS. 7A-7F. The user can move the stethoscope chestpiece and echo device 252 across the patient, while the portable electronic device 266 can receive the transducer data from the echo device 252, and use its own processor and display and mobile app to provide all data processing (e.g., determining peak blood flows), comparisons (e.g., to blood flow thresholds), and visual/audio indicia of peak blood flow (e.g., risk assessments, number representing peak blood flow speed, etc.).

Other embodiments of the device are also within the scope of the invention, such as a device similar to that of FIGS. 7B-7D but configured to be secured in other ways to the stethoscope chestpiece, such as a device configured to be snapped over the upper surface and/or lower (e.g., diaphragm) surface of a stethoscope chestpiece.

Note that the system may include one or more alarm functions, such as where alarms are activated if the peak measured blood flow velocity reaches one or more designated values. For example, the green, yellow, and red lights discussed previously with respect to FIGS. 4B and 4C may constitute alarm signals. Other alarm signals are also within the scope of the invention, including acoustic alarms, visual alarms (e.g., flashing lights), vibration alarms, etc. For example, the device may be configured to vibrate each time that a newly-recorded maximum peak velocity exceeds a not-previously-reached threshold for one of the increased risk levels (e.g., mild, moderate, high).

Unless otherwise noted, all technical and scientific terms used herein have the same meaning as commonly understood by one of ordinary skill in the art to which this disclosure belongs. In order to facilitate review of the various embodiments of the disclosure, the following explanation of terms is provided:

The singular terms "a", "an", and "the" include plural referents unless context clearly indicates otherwise. The term "or" refers to a single element of stated alternative elements or a combination of two or more elements, unless context clearly indicates otherwise.

The term "includes" means "comprises." For example, a device that includes or comprises A and B contains A and B, but may optionally contain C or other components other than A and B. Moreover, a device that includes or comprises A or B may contain A or B or A and B, and optionally one or more other components, such as C.

The term "subject" refers to both human and other animal subjects. In certain embodiments, the subject is a human or other mammal, such as a primate, cat, dog, cow, horse, rodent, sheep, goat, or pig. In a particular example, the subject is a human patient.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

Although methods and materials similar or equivalent to those described herein can be used in the practice or testing of the present disclosure, suitable methods and materials are described above. In case of conflict, the present specification, including terms, will control. In addition, the materials, methods, and examples are illustrative only and not intended to be limiting.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

What is claimed is:

1. A method of screening a heart of a patient for heart valve disease, comprising:
    determining peak blood flow velocity within the heart using a hand-held echo velocity monitoring device held by a user against the patient;
    comparing the peak blood flow velocity to a first screening threshold blood flow velocity value;
    if the peak blood flow velocity is below the first screening threshold blood flow velocity value, then providing a first visual indicia through a visual display comprising a green light, the first screening threshold blood flow velocity value indicating a mild risk velocity threshold for heart valve disease and the patient is not provided with additional heart valve disease assessment and analysis using equipment other than the hand-held echo velocity monitoring device;
    if the peak blood flow velocity exceeds the first screening threshold blood flow velocity value, then comparing the peak blood flow velocity to a second screening threshold blood flow velocity value;
    if the peak blood flow velocity matches or exceeds the second screening threshold blood flow velocity value and is below a third screening threshold blood flow velocity value, then providing a second visual indicia through the visual display comprising a yellow light, the second screening threshold blood flow velocity value indicating a moderate risk velocity threshold for heart valve disease;
    if the peak blood flow velocity exceeds the second screening threshold blood flow velocity value, then comparing the peak blood flow velocity to the third screening threshold blood flow velocity value;
    if the peak blood flow velocity matches or exceeds the third screening threshold blood flow velocity value, then providing a third visual indicia through the visual display comprising a red light, the third screening threshold blood flow velocity value indicating a high risk velocity threshold for heart valve disease and providing a recommendation via the hand-held echo velocity monitoring device that the patient receives the additional heart valve disease assessment and analysis using equipment other than the hand-held echo velocity monitoring device;
    wherein the first screening threshold blood flow velocity value is 2.5 m/s;
    wherein the second screening threshold blood flow velocity value is 3.0 m/s; and
    wherein the third screening threshold blood flow velocity value is 4.0 m/s.

2. The method of claim 1, wherein determining peak blood flow velocity within the heart comprises moving the hand-held echo velocity monitoring device across multiple positions on chest and/or abdominal areas of the patient and determining blood flow velocities while the hand-held echo velocity monitoring device is at each of the multiple positions.

3. The method of claim 1, wherein the additional heart valve disease assessment and analysis comprises at least one of the following: heart valve imaging via echocardiogram; heart valve imaging via magnetic resonance imaging (MRI); cardiac catheterization; stress testing; electrocardiogram (EKG); and chest x-ray.

4. The method of claim 1, wherein the additional heart valve disease assessment and analysis comprises providing an image of heart valve structures such as a heart valve orifice and/or heart valve leaflets.

* * * * *